(12) United States Patent
Lake et al.

(10) Patent No.: US 8,498,689 B2
(45) Date of Patent: Jul. 30, 2013

(54) REAL TIME MOTION INFORMATION CAPTURE IN AN MRI ENVIRONMENT

(75) Inventors: David S. Lake, Rochester, MN (US); Armando Manduca, Rochester, MN (US); Jeffrey S. McAllister, St. Paul, MN (US); Nelson Ramirez, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 773 days.

(21) Appl. No.: 12/612,143

(22) Filed: Nov. 4, 2009

(65) Prior Publication Data

US 2011/0105883 A1 May 5, 2011

(51) Int. Cl.
*A61B 5/05* (2006.01)

(52) U.S. Cl.
USPC .......................................... 600/414; 600/415

(58) Field of Classification Search
USPC ................... 600/410, 413, 411, 424, 426, 428
See application file for complete search history.

(56) References Cited

U.S. PATENT DOCUMENTS

| | | | |
|---|---|---|---|
| 5,630,422 A * | 5/1997 | Zanakis | 600/473 |
| 6,405,072 B1 * | 6/2002 | Cosman | 600/426 |
| 6,480,111 B2 * | 11/2002 | Canady et al. | 340/573.1 |
| 7,952,079 B2 * | 5/2011 | Neustadter et al. | 250/393 |
| 2008/0194942 A1 * | 8/2008 | Cumpson et al. | 600/415 |
| 2011/0098574 A1 * | 4/2011 | Hwang et al. | 600/473 |

* cited by examiner

*Primary Examiner* — Parikha Mehta
(74) *Attorney, Agent, or Firm* — Patterson & Sheridan LLP (57) ABSTRACT

Systems, methods and articles of manufacture are disclosed for capturing motion information in a magnetic resonance imaging (MRI) environment. A light sink in the MRI environment may detect light emitted from a plurality of light sources. Each of the plurality of light sources may emit light of a different frequency. Further, each of the plurality of light sources may be located at a different spatial position in the MRI environment. The detected light may be analyzed. A change in spatial position of the light sink may be computed based on the analysis.

24 Claims, 7 Drawing Sheets

REAL TIME MOTION INFORMATION CAPTURE IN AN MRI ENVIRONMENT

STATEMENT REGARDING FEDERALLY SPONSORED RESEARCH OR DEVELOPMENT

This invention was made with government support under EB000229 awarded by the National Institute of Biomedical Imaging and Bioengineering. The government has certain rights in the invention.

BACKGROUND OF THE INVENTION

1. Field of the Invention

Embodiments of the invention capture motion information regarding movement of a test subject. More specifically, embodiments of the invention capture motion information for a test subject in a magnetic resonance imaging (MRI) device.

2. Description of the Related Art

Real time motion information capture may be used for various applications in an MRI environment. For example, head motion of a patient during an MRI brain scan may degrade image quality of the scan. Real time motion information capture may be used to correct any such head motion of the patient.

However, real time motion information capture in an MRI environment presents several distinct challenges. Because metal and electronic objects may interfere with the magnetic field of an MRI unit, electronic video equipment (such as video cameras) must be mounted far away from a patient in the MRI environment. Tracking objects may also be placed on a patient's body to aid video capture. Because video cameras must be mounted far away from a patient in the MRI environment, the captured footage may be of insufficient resolution to accurately determine patient motion. Further, video-based approaches require extensive computation (e.g., a large amount of video processing) to determine patient motion.

An alternative to video-based approaches is post-processing approaches. That is, patient motion may be corrected during post-processing of image data. However, post-processing approaches may not take into account any measurements of patient motion. Further, post-processing approaches may only correct certain types of motion, such as translational motion.

SUMMARY OF THE INVENTION

One embodiment of the invention includes a method for capturing motion information in a magnetic resonance imaging (MRI) environment, comprising configuring one or more computer processors to perform an operation. The operation may generally include detecting, by a light sink in the MRI environment, light emitted from a plurality of light sources, wherein each of the plurality of light sources emit light of a different frequency, wherein each of the plurality of light sources is located at a different spatial position in the MRI environment, and wherein the light sink is detachably fastened to a subject; analyzing the detected light to determine, by operation of the one or more computer processors, a change in spatial position of the light sink; and computing a change in spatial position of the subject during an MRI scan based on a computed change in spatial position of the light sink.

Another embodiment of the invention includes a computer-readable storage medium containing a program, which when executed by the processor is configured to perform an operation for capturing motion information in a magnetic resonance imaging (MRI) environment. The operation may generally include detecting, by a light sink in the MRI environment, light emitted from a plurality of light sources, wherein each of the plurality of light sources emit light of a different frequency, wherein each of the plurality of light sources is located at a different spatial position in the MRI environment, and wherein the light sink is detachably fastened to a subject; analyzing the detected light to determine, by operation of the one or more computer processors, a change in spatial position of the light sink; and computing a change in spatial position of the subject during an MRI scan based on a computed change in spatial position of the light sink.

Still another embodiment of the invention includes a system having a processor and a memory containing a program, which when executed by the processor is configured to perform an operation for capturing motion information in a magnetic resonance imaging (MRI) environment. The operation may generally include detecting, by a light sink in the MRI environment, light emitted from a plurality of light sources, wherein each of the plurality of light sources emit light of a different frequency, wherein each of the plurality of light sources is located at a different spatial position in the MRI environment, and wherein the light sink is detachably fastened to a subject; analyzing the detected light to determine, by operation of the one or more computer processors, a change in spatial position of the light sink; and computing a change in spatial position of the subject during an MRI scan based on a computed change in spatial position of the light sink.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Embodiments of the present invention generally capture motion information in an MRI machine. One embodiment of the invention provides light sources, at least one light sink, and a motion detector. In one embodiment, the light sink may detect light emitted from the light sources in a magnetic resonance imaging (MRI) machine. The light sources may each emit light at a different frequency. Further, each light source may be located at a different spatial position in the MRI machine. The motion detector may analyze the detected light. For example, the motion detector may compute a change in spatial position of the light sink based on the different frequencies, and/or the different spatial positions. The motion detector may also compute a change in spatial position of a subject of an MRI scan, to which one or more light sinks are secured, based on the computed changes in spatial positions of one or more light sinks. Further, the motion detector may compute spatial positions of one or more light sinks or the subject. Because spatial positions are determined based on an analysis (e.g., a Fast Fourier Transform) of one-dimensional signals, motion information may be captured efficiently (e.g., in real time). Further, changes in spatial positions (i.e., motion) of the subject may be determined accurately and at a high resolution. Further still, changes in the motion of a subject may be determined at the time of an MRI scan (i.e., "instrascan") or following the MRI scan (i.e., post-processing).

If the captured motion information reveals that motion of a subject exceeds a predefined tolerance threshold, the MRI scan may be repeated. Further, the captured motion information may be combined with post-processing approaches to further improve motion correction of images generated from an MRI scan.

In one embodiment, each light sink and light source is an open end of an optical fiber cable. Each optical fiber cable sends and receives light information within the MRI environment. Other media not affected by high strength magnetic fields of an MRI environment (i.e., other than fiber optics) may be supported by embodiments of the invention. For example, each emitter may emit a different signal (e.g., wireless signals). Changes in the motion of a subject may be determined based on differing times with which each of the emitted signals are detected by a detector.

Furthermore, while embodiments herein are described with reference to detecting motion in an MRI environment, other application domains and environments are broadly contemplated. For example, the motion detector 150 may detect motion in application domains of machine vision for industrial vision applications and of 3D motion capture systems for gaming applications.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

One embodiment of the invention is implemented as a program product for use with a computer system. The program(s) of the program product defines functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present invention, are embodiments of the present invention. Other media include communications media through which information is conveyed to a computer, such as through a computer or telephone network, including wireless communications networks. The latter embodiment specifically includes transmitting information to/from the Internet and other networks. Such communications media, when carrying computer-readable instructions that direct the functions of the present invention, are embodiments of the present invention. Broadly, computer-readable storage media and communications media may be referred to herein as computer-readable media.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

Figure 1A:
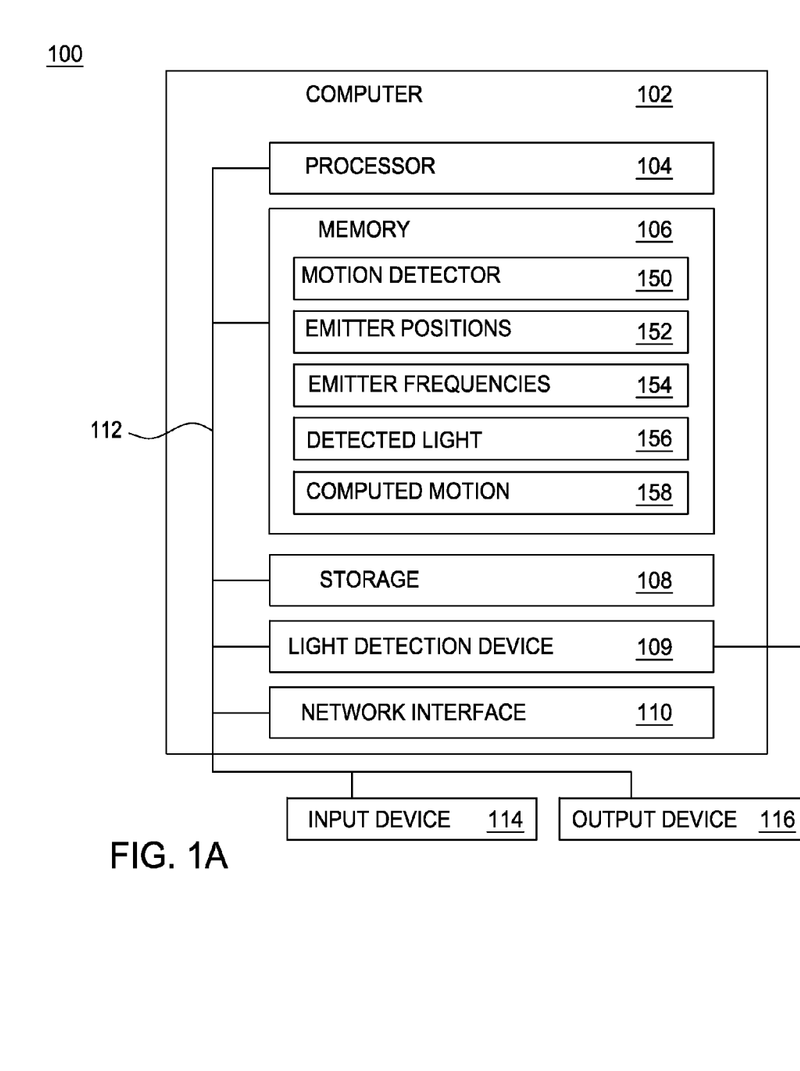
FIG. 1 is a block diagram illustrating a system for capturing motion information in an MRI environment, according to one embodiment of the invention.
Figure 1B:
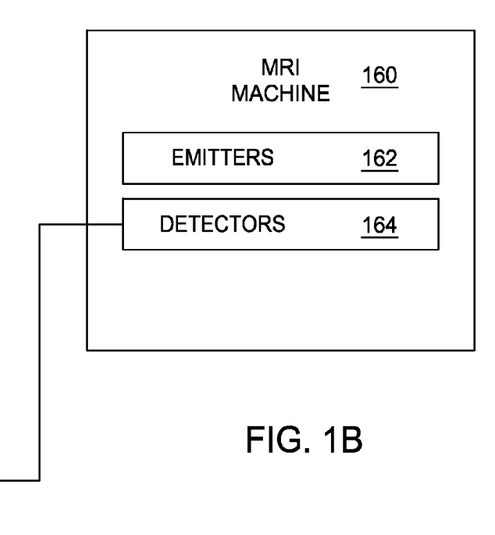

FIG. 1 is a block diagram illustrating a system 100 for capturing motion information in an MRI environment, according to one embodiment of the invention. The system 100 includes a computer 102 and an MRI machine 160. The computer 102 may be connected to other computers via a network (not shown). In general, the network may be a telecommunications network and/or a wide area network (WAN). In a particular embodiment, the network is the Internet.

The computer 102 generally includes a processor 104 connected via a bus 112 to a memory 106, a network interface device 110, a storage 108, an input device 114, and an output device 116. The computer 102 is generally under the control of an operating system (not shown). Examples of operating systems include UNIX, versions of the Microsoft Windows® operating system, and distributions of the Linux® operating system. (Note: Linux is at trademark of Linus Torvalds in the United States and other countries.) More generally, any operating system supporting the functions disclosed herein may be used. The processor 104 is included to be representative of a single CPU, multiple CPUs, a single CPU having multiple processing cores, and the like. Similarly, the memory 106 may be a random access memory. While the memory 106 is shown as a single entity, it should be understood that the memory 106 may comprise a plurality of modules, and that the memory 106 may exist at multiple levels, from high speed registers and caches to lower speed but larger DRAM chips. The network interface device 110 may be any type of network communications device allowing the computer 102 to communicate with other computers via the network 130.

The input device 114 may be any device for providing input to the computer 102. For example, a keyboard, keypad, light pen, touch-screen, track-ball, or speech recognition unit, audio/video player, and the like may be used. The output device 116 may be any device for providing output to a user of the computer 102. For example, the output device 116 may be any conventional display screen or set of speakers, along with their respective interface cards, i.e., video cards and sound cards (not shown). Although shown separately from the input device 114, the output device 116 and input device 114 may be combined. For example, a display screen with an integrated touch-screen, a display with an integrated keyboard, or a speech recognition unit combined with a text speech converter may be used.

The storage 108 may be a hard disk drive storage device. Although the storage 108 is shown as a single unit, the storage 108 may be a combination of fixed and/or removable storage devices, such as fixed disc drives, floppy disc drives, tape drives, removable memory cards, or optical storage. The memory 106 and the storage 108 may be part of one virtual address space spanning multiple primary and secondary storage devices.

The light detection device 109 may be any device for measuring frequency of light detected by the detectors 164 and providing measured frequencies to the computer 102. Although the light detection device 109 is shown as a device internal to the computer 102, the light detection device 109 may also be a device peripheral to the computer 102. Other ways of providing frequency information to the computer 102 of light detected by the detectors 164 are broadly contemplated. For example, the light detection device 109 may be part of the MRI machine 160, or may be a standalone device. Further, the computer 102 may receive light frequency information via any communications interface, e.g., ATA (Advanced Technology Attachment) or SATA (Serial ATA) interconnects, PCI (Peripheral Component Interconnect) or PCIe (PCI Express) interconnects, serial or parallel interconnects, USB (Universal Serial Bus) interconnects, IEEE-1394 interconnects, telephone interconnects, Ethernet interconnects, wireless interconnects, etc.

The terms "light source" and "light sink" may also be described herein as "emitter" and "detector", respectively. As shown, the memory 106 of the computer 102 includes a motion detector 150, emitter positions 152, emitter frequencies 154, detected light 156 (or more specifically, data representing the detected light), and a computed motion 158. Further, the MRI machine 160 includes a plurality of emitters 162 and one or more detectors 164. The plurality of emitters 162 and the one or more detectors 164 are further described in conjunction with FIGS. 2 through 8. Further, FIGS. 2 through 8 and associated descriptions detail the structure and operation of the motion detector 150 running on the computer 102.

Figure 2:
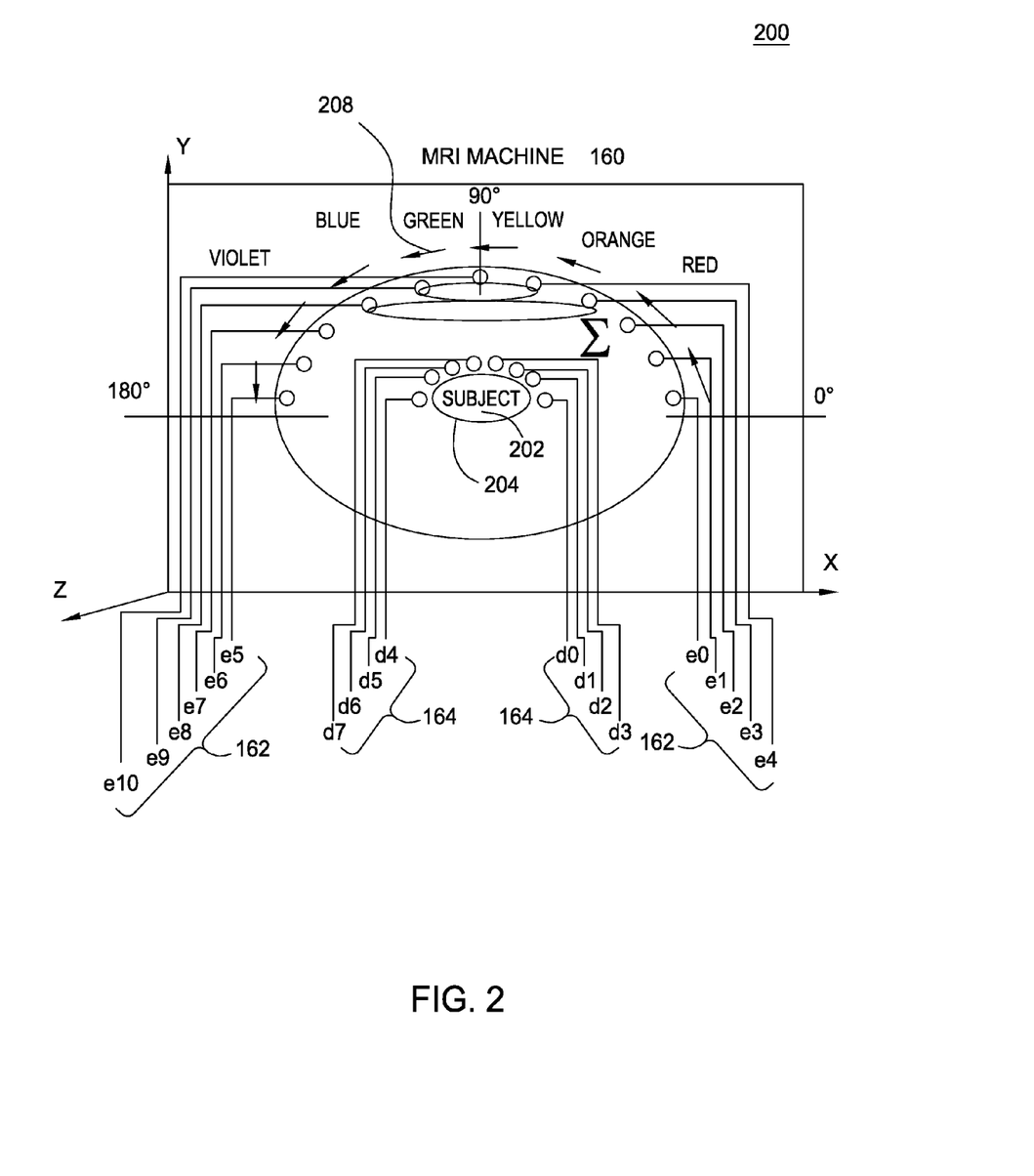
FIG. 2 is a longitudinal, cross-sectional diagram of an MRI machine, according to one embodiment of the invention.

FIG. 2 is a longitudinal, cross-sectional diagram 200 of the MRI machine 160 of FIG. 1, according to one embodiment of the invention. As shown, a subject (or body) 202 is undergoing an MRI scan by the MRI machine 160. More generally, the subject 202 may be any variety of living or non-living material. Thus, references herein to a human patient are merely illustrative, and not intended to be limiting of the invention. For example, the subject may be any living organism, such as an animal.

Illustratively, the MRI machine 160 includes emitters 162 (labeled e0 through e10) and one or more detectors 164 (labeled d0 through d7). As shown, the one or more detectors 164 may be connected to a coupler 204. In one embodiment, the coupler 204 includes non-electronic, non-metallic material that may connect to the one or more detectors 164 and with the subject 202. For example, the coupler 204 may be a plastic headband or visor, an adhesive patch, or a handheld plastic member, etc. In one embodiment, the coupler 204 may not be needed. For example, if the one or more detectors 164 include an open end of an optical fiber cable, a subject may undergo an MRI wrist scan while holding the optical fiber cable.

In one embodiment, the motion detector 150 may use the plurality of emitters 162 and the one or more detectors 164 to calculate spatial positions (and/or changes thereof) of a subject during an MRI scan. For example, the motion detector 150 may perform a frequency to position mapping, i.e., the motion detector 150 may map a frequency of light detected by the one or more detectors 164 to a spatial position of the subject 202.

In one embodiment, the emitters 162, the detectors 164, and the coupler 204 each include material that may be placed directly on a body part of a subject being imaged in an MRI environment without interfering with the magnetic field of the MRI machine 160. Each emitters 162 may be an open end (or tip) of an optical fiber cable, according to one embodiment. That is, the end of the optical fiber cable may be open to allow light to exit. The emitters 162 may be arranged different spatial positions 152 in the MRI environment. For example, the emitters 162 may be arranged radially from 0 degrees to 180 degrees along the interior of an MRI machine 160 (relative to the subject 202). Further, each emitter may include a non-metallic lens coupling assembly to focus emitted light into a narrow beam. Similarly, each detector may include a non-metallic lens coupling assembly to improve an ability of the respective detector to detect emitted light. Further still, the emitters 162 may be arranged via increasing frequency of light in the MRI environment. In other words, the frequency 154 of each emitter 162 may be a function of radial position of the respective emitter 162, according to one embodiment. For example, the motion detector 150 may define an axis for the plurality of emitters 162 in the MRI environment, such that each of the plurality of emitters 162 projects onto a different point on the defined axis. The motion detector 150 may then configure the plurality of emitters 162 to emit light of increasing (or decreasing) frequency 154 along the defined axis (e.g., the x-axis of FIG. 2).

As shown by arrows 208, the emitters 162 emit light ranging from red, orange, yellow, green, blue, and violet. Further, although embodiments herein are described with reference to the plurality of emitters 162 emitting light having wavelengths within a visible spectrum (that is, the portion of the electromagnetic spectrum that may be detected by a human eye), other embodiments are broadly contemplated. For example, the plurality of emitters 162 may emit light having wavelengths falling outside of the visible spectrum. Further, the detectors 164 may detect electromagnetic radiation of any wavelength, whether visible or not. In another embodiment, the plurality of emitters 162 need not be configured to emit light of increasing (or decreasing) frequency 154 along any defined axis. That is, the plurality of emitters 162 may merely provide a distinct 3D-position-to-frequency mapping. In one embodiment, the motion detector 150, in determining motions of the subject, may also take into account any discrepancy in intensity of light emitted from the emitters 162. In another embodiment, each emitter 162 may emit light of the same (constant) intensity.

Each of the one or more detectors 164 may be an open end of an optical fiber cable. That is, the end of the optical fiber cable may be open to allow light to enter. The one or more detectors 164 may be operably connected to the light detection device 109 via any non-metallic, non-electronic medium, according to one embodiment. Further, the motion detector 150 may determine 3D motion of the subject based on one detector 164. Additional detectors 164 may serve as redundancy, according to one embodiment. For example, the motion detector 150 may analyze light 156 detected from additional detectors 164 to validate and/or refine a computed motion 158.

Figure 3A:
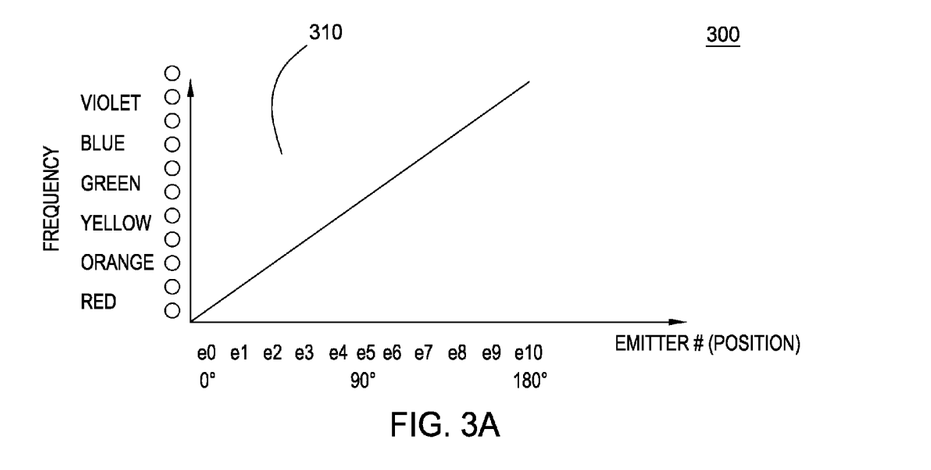
FIGS. 3A-3C illustrate diagrams for analyzing light detected by one or more detectors disposed within an MRI machine, according to one embodiment of the invention.
Figure 3B:
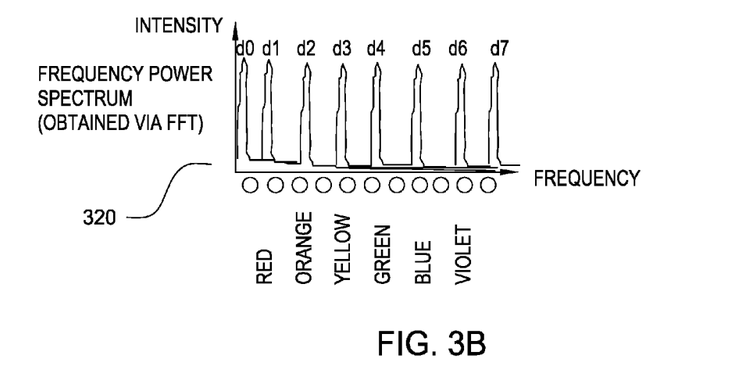
Figure 3C:
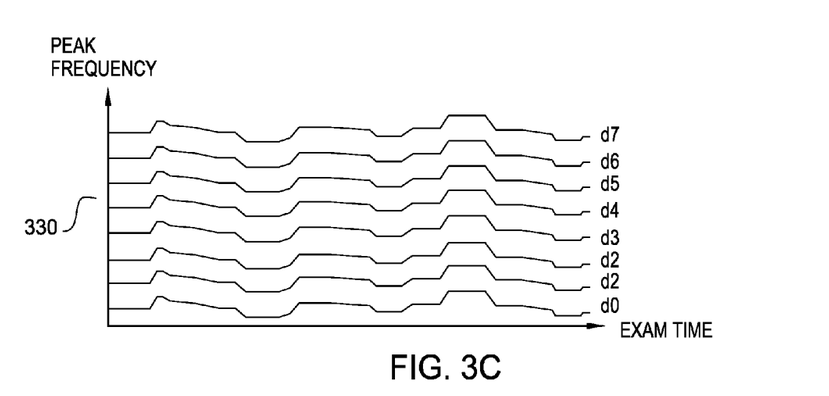

FIGS. 3A-3C illustrate diagrams 300 for analyzing light 156 detected by the one or more detectors 164. The analyses may be performed by the motion detector 150 of FIG. 1. The diagrams are merely illustrative and are not intended to be limiting of the invention. The diagrams 300 include an emitter-to-frequency graph 310 of FIG. 3A, a power spectrum graph 320 of FIG. 3B, and a time-to-frequency graph 330 of FIG. 3C.

As shown in FIG. 3A, the emitter-to-frequency graph 310 associates each of the plurality of emitters 162 with a frequency 154 and a position 152. In this particular example, the position 152 is expressed in degrees, based on the position of the subject 204 and an interior arc of the MRI machine 160. In one embodiment, the motion detector 150 defines the frequencies 154, positions 152, and associated emitters 162 based on user input. In another embodiment, the motion detector 150 receives information about predefined frequencies 154, positions 152, and associated emitters 162.

As shown in FIG. 3B, the power spectrum graph 320 shows frequencies and associated intensities of light detected at the one or more detectors 164. In one embodiment, the motion detector 150 may generate the power spectrum graph 320 by performing an FFT on the light 156 detected by the one or more detectors 164. Further, as shown by the power spectrum graph 320, the detected light 156 may include light from the plurality of emitters 162, mixed together in different intensities. Further, peak frequencies (i.e., frequencies with maximum energy) in the power spectrum graph 320 indicate the proximity of a detector 164 to the peak frequencies. In one embodiment, the motion detector 150 may accurately determine motion of the one or more detectors 164 (relative to the plurality of emitters 162) based on changes to the peak frequencies over time. The motion detector 150 may also perform triangulation to determine an exact position (i.e., 3D coordinate in the MRI environment) of the detector 164. For example, the motion detector 150 may determine a spatial distance from each detector 164 from each of the plurality of light sources. The motion detector 150 may then determine an exact position of the detector 164 by computing an intersection of the spatial distances from the plurality of emitters 162. Thus, peak frequency changes of light 156 detected by each detector 164 indicate movement of the detector (and thus movement of the subject 202).

As shown in FIG. 3C, the time-to-frequency graph 330 maps peak frequencies of each detected light 156 to time. That is, the time-to-frequency graph 330 shows changes of the peak frequencies over time (e.g., during an MRI scan of the subject 202). Any movement of the subject 202 during the MRI scan may also cause each detector 164 to move accordingly. As each detector 164 moves (as a result of subject 202 movement) from an old spatial position into a new spatial position, each detector 164 may detect a different composition of light 156 from the different emitters in the new spatial position, compared to the old spatial position. The different composition of light 156 detected may include a different intensity of light emitted from one or more of the plurality of emitters 162, due to the new spatial position of the detector 164. The motion detector 150 may analyze the detected light 156 (e.g., via an FFT, etc.) to determine a corresponding change in peak frequency of the detected light, as illustrated the time-to-frequency graph 330. Further, if the emitters 162 are positioned at fixed locations in the MRI environment, the motion detector 150 may also map the changes in peak frequency to positional changes of a detector 164.

FIGS. 4A-4D illustrates diagrams 400 for 3D motion determination based on the received light 156, according to one embodiment of the invention. The motion detector 150 of may make the 3D motion determination, according to one embodiment. The diagrams are merely illustrative and are not intended to be limiting of the invention. The diagrams 400 include a 3D position graph 410 of FIG. 4A and movement graphs 422, 424, 426 of FIGS. 4B-4D, respectively.

Figures 4A, 4B, 4C, 4D:
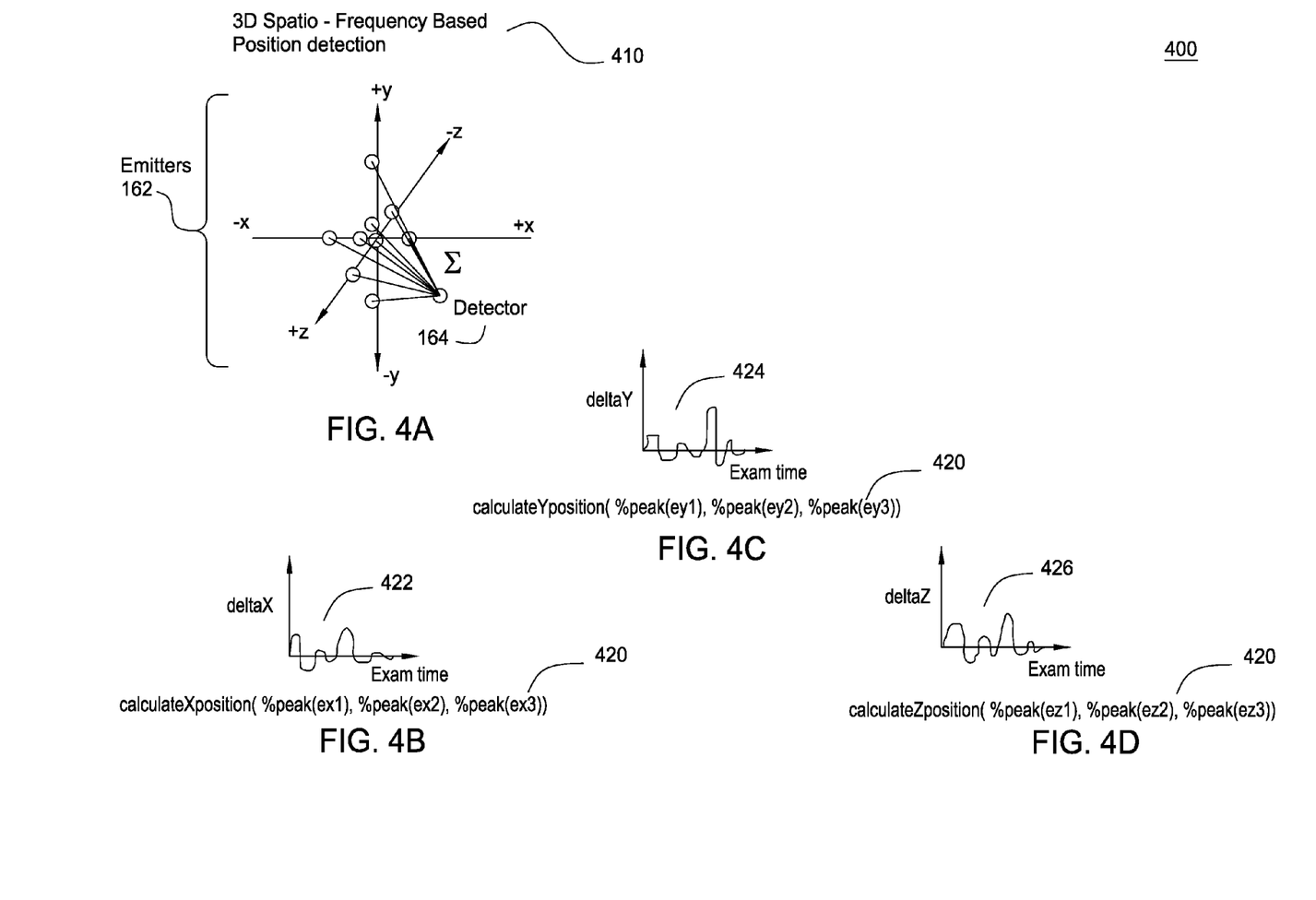
FIGS. 4A-4D illustrate diagrams for 3D motion determination based on light received by the one or more detectors, according to one embodiment of the invention.

As shown in FIG. 4A, the 3D position graph 410 illustrates a spatial position (specifically, the 3D coordinates thereof) of a detector 164 relative to a plurality of emitters 162. In one embodiment, the motion detector 150 may determine the spatial position of the detector 164 on the 3D position graph 410 based on the detected light 156. That is, movement of the detector 164 (e.g., as a result of subject 202 movement) may result in a change in composition of the detected light 156 (e.g., an increase or decrease in intensity of light detected from an emitter 162). The motion detector 150 may determine a change in the spatial position of the detector 164 based on the change in composition of the detected light 156.

As shown in FIGS. 4B-4D, the movement graphs 422, 424, 426 show changes in spatial position of a detector 164 with respect to an x-axis, a y-axis, and a z-axis of the 3D coordinate system of an MRI environment, respectively. In one embodiment, the plurality of emitters 162 are arranged such that there are at least three sources of distinct frequencies (e.g., colors of light emitted by emitters 162) along each axis of the 3D coordinate system (such as shown in the 3D position graph 410). In one embodiment, the motion detector 150 may apply FFT signal decomposition to the detected light 156 to generate a frequency spectrum showing an amount of energy in each frequency of the frequency spectrum. The motion detector 150 may then determine a spatial distance between the detector 164 and each of the plurality of emitters 162 and generate a exact 3D coordinates representing the spatial position of the detector 164. That is, as a detector 164 moves away from a given emitter 162, the frequency component of the detected light 156 emitted from the emitter 162 decreases in intensity. The frequency component of the detected light 156 refers to light emitted by a single emitter 162 and detected by the detector 164. In other words, changes in frequency components detected by the detector 164 in the light 156 indicate movement of the detector 164 with respect to the emitters 162.

Further, the movement graphs 422, 424, and 426 show functions for calculating 3D coordinates for a detector 164. As shown, the functions include calculateXposition ( ), calculateYposition ( ), and calculateZposition ( ). The functions are merely illustrative and are not intended to be limiting of the invention. The motion detector 150 may use calculateXposition ( ) to compute a first coordinate (e.g., along the x-axis) of the detector 164, based on peak frequencies of light 156 detected from the emitters 164 located along the x-axis. Further, the motion detector 150 may use calculateYposition ( ) to compute a second coordinate (e.g., along the y-axis) of the detector 164, based on peak frequencies of light 156 detected from the emitters 164 located along the y-axis. The motion detector 150 may also use calcualteZposition ( ) to compute a third coordinate (e.g., along the z-axis) of the detector 164, based on peak frequencies of light 156 detected from the emitters 164 located along the z-axis.

Figure 5:
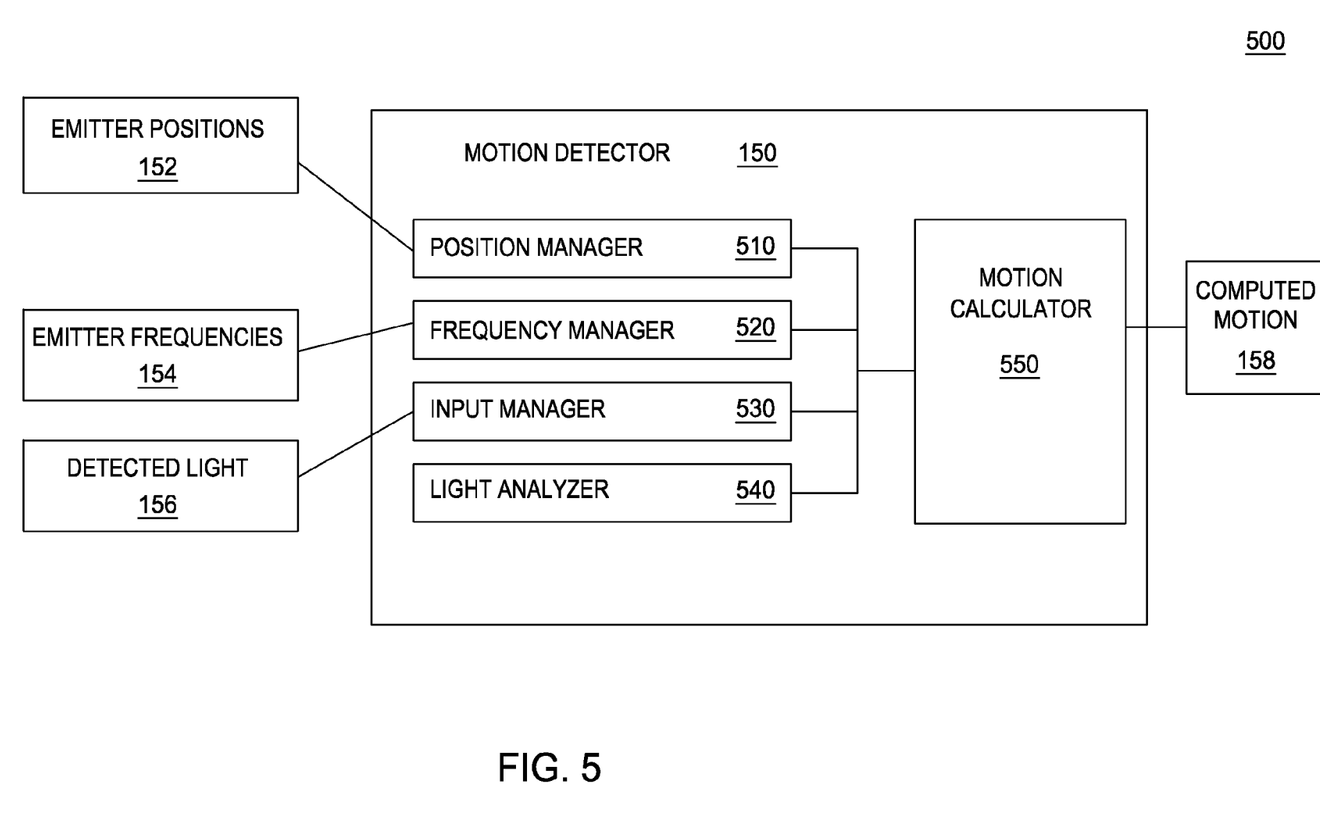
FIG. 5 is a block diagram illustrating components of a motion detector, according to one embodiment of the invention.

FIG. 5 is a block diagram 200 illustrating components of the motion detector 150 of FIG. 1, according to one embodiment of the invention. As shown, the motion detector 150 includes a position manager 510, a frequency manager 520, an input manager 530, a light analyzer 540, and a motion calculator 550.

In one embodiment, the position manager 510 configures emitter positions 152. For example, the position manager 510 may receive user input specifying positions for the emitters in the MRI environment. Each position 152 may specify a 3D spatial coordinate position for one of the emitters within the MRI environment. Further, the frequency manager 520 may receive emitter frequencies 154. And each emitter frequency 154 may be associated with one of the emitter positions 152. Each emitter frequency 154 associated with an emitter position 152 represents a frequency of light emitted by an emitter at the emitter position 152. For example, the frequency manager 520 may receive a frequency of (red) light associated with e0 of FIG. 2.

In one embodiment, the input manager 530 receives data representing the light 156 detected by the one or more detectors 164. The data may be any representation of the light 156 sufficient to describe the composition of the light 156 (e.g., a plurality of component frequencies and associated intensities). Further, the light analyzer 540 evaluates the detected light 156. For example, the light analyzer 540 may use Fourier analysis to decompose the detected light 156 into a power spectrum (e.g., by performing an FFT on a time-domain representation of the light 156). For instance, the light analyzer may generate the power spectrum graph 320 of FIG. 3B.

In one embodiment, the motion calculator 550 computes motion 158 of a detector 164. For example, the motion calculator 550 may compute a change (represented in 3D coordinates) in position of a detector 164, based on analyzing the detected light 156. The motion calculator 550 may also compute an absolute position of a detector 164 in the 3D coordinate system, based on analyzing the detected light 156. For example, the motion calculator 550 may compute an intersection of the spatial distances from the plurality of emitters 162. Further, the motion calculator 550 may also compute a motion 158 of the subject 202 based on the computed motions 158 of one or more detectors 164, according to one embodiment.

Figure 6:
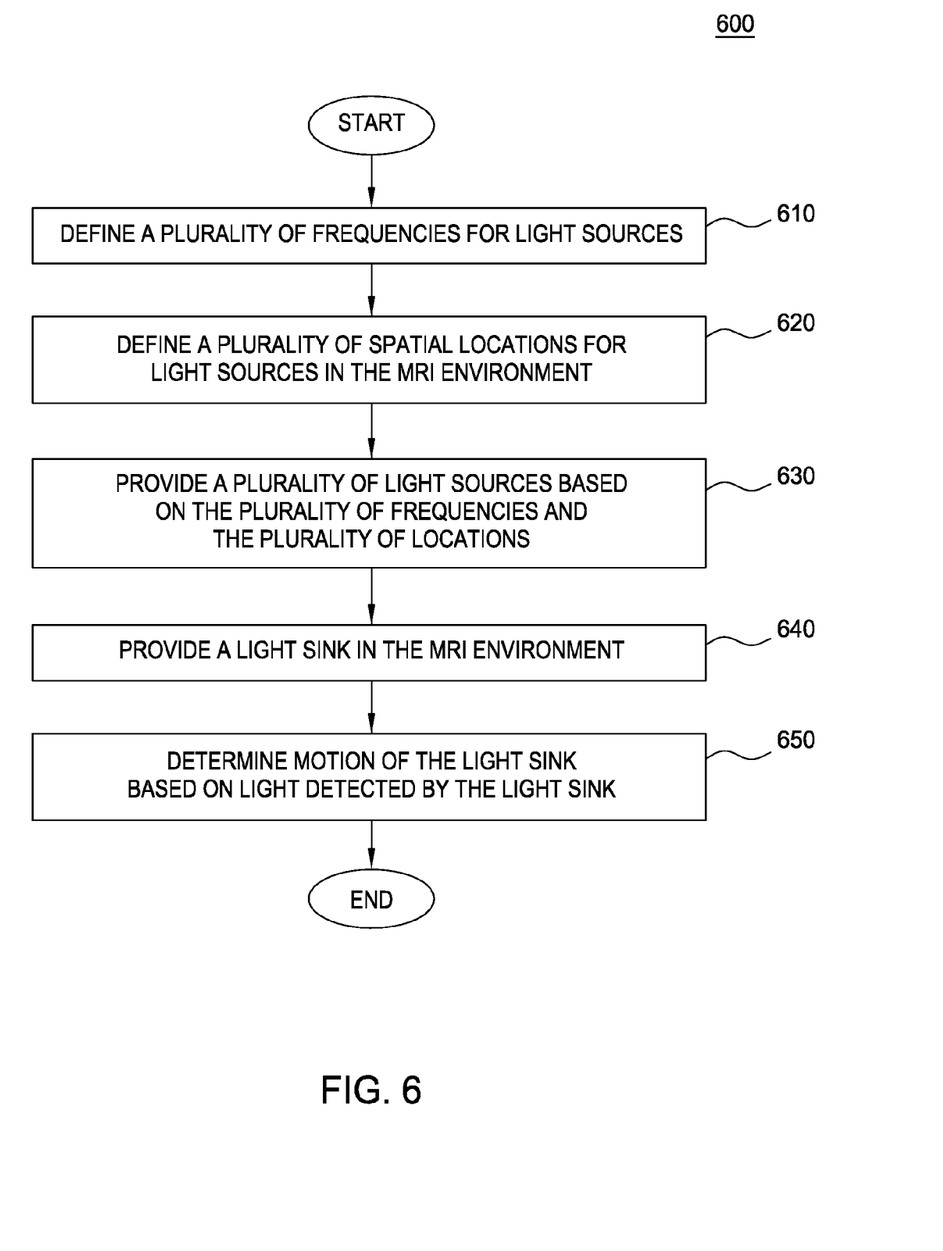
FIG. 6 is a flowchart depicting a method for detecting motion in an MRI machine, according to one embodiment of the invention.

FIG. 6 is a flowchart depicting a method 600 for detecting motion in an MRI environment, according to one embodiment of the invention. The method 600 may be performed by the motion detector 150 of FIG. 1.

As shown, the method 600 begins at step 610, where frequencies are defined for the light sources (i.e., emitters) 162. For example, the motion detector 150 may include graphical interface components allowing the user to define what frequencies are, in fact, emitted by a given emitter. At step 620, the motion detector 150 defines a plurality of spatial locations (i.e., emitter locations) 152 for the light sources 162 in the MRI environment. For example, the motion detector 150 may define the spatial locations 152 of the emitter-to-frequency graph 310 of FIG. 3A. In one embodiment, the motion detector 150 may also define the plurality of spatial locations 152 based on user input. In one embodiment, the spatial locations 152 may also be specific to (e.g., suitable for) a type of body part of a patient (e.g., head, arm, etc.).

At step 630, the motion detector 150 provides a plurality of light sources 162 having the plurality of frequencies 154 and at the plurality of spatial locations 152. For example, the motion detector may provide the emitters 162 as arranged in the MRI machine 160 of FIG. 2. At step 640, the light sink 164 may be affixed to an MRI subject. Further, the emitters 162 and light sink 164 may be calibrated (i.e., prior to an MRI scan), according to one embodiment. Specifically, the motion detector 150 may compute a "motion free" signal from analyzing light detected by the light sink 164 (i.e., light emitted from the light sources 162). The motion detector 150 may then compute a relative motion based on variation of a received signal (detected by the light sink 164) from the computed "motion free" signal. Further, the motion detector 150 may also compute non-rigid body motions, according to one embodiment. For example, during breathing, the abdomen of a patient may have uneven movement at different regions of the abdomen. Light sinks 164 may be placed at the abdomen of the patient to detect light 156. The motion detector 150 may determine a motion of the abdomen of the patient based on the detected light 156.

At step 650, the motion detector 150 determines motion of the light sink 164 based on the light 156 detected by the light sink 164. For example, the motion detector 150 may determine a motion of the light sink 164 (e.g., as shown in movement graphs 422, 424, 426 of FIGS. 4B-4D) based on analyzing the detected light 156 (e.g., as shown in the power spectrum graph 320 and the time-to-frequency graph 330 of FIG. 3C). Step 650 is further described below in conjunction with FIG. 7. After step 650, the method 600 terminates.

Figure 7:
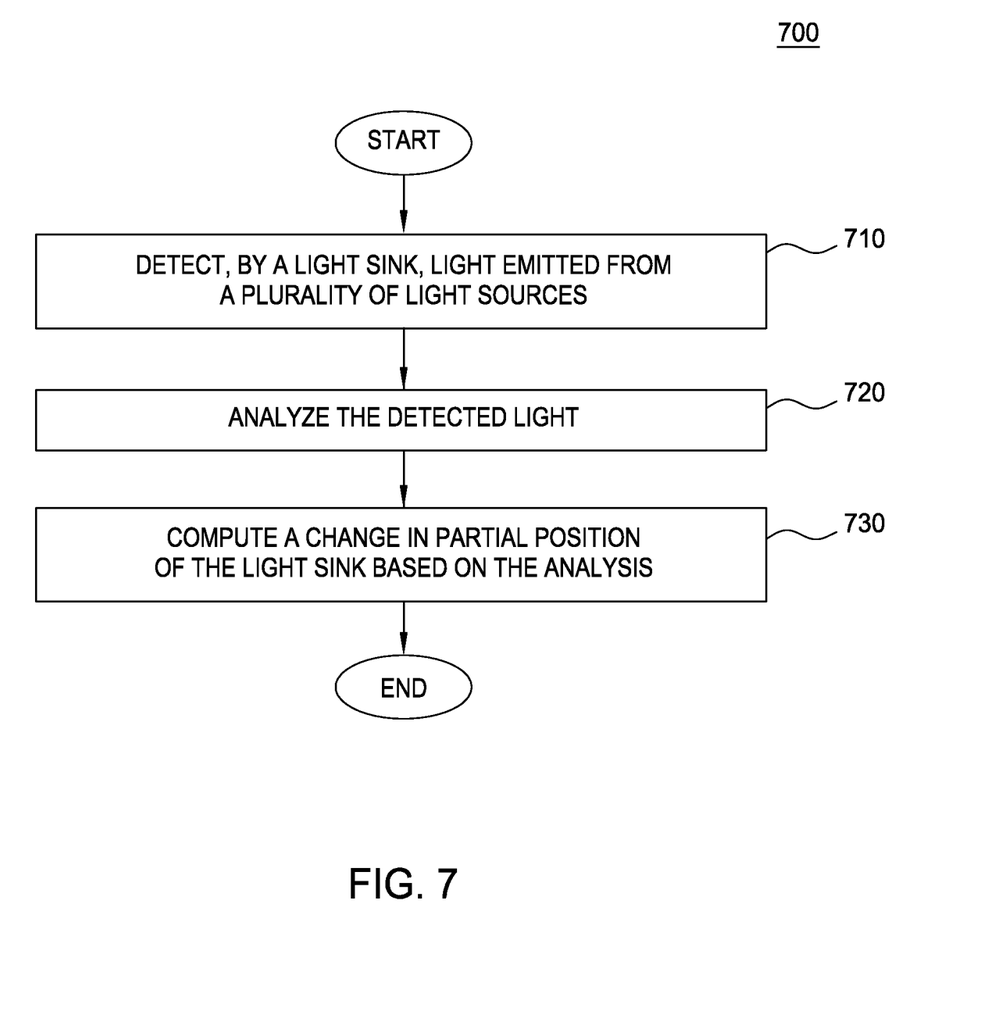
FIG. 7 is a flowchart depicting a method for capturing motion information in an MRI machine, according to one embodiment of the invention.

FIG. 7 is a flowchart depicting a method 700 for capturing motion information in an MRI environment, according to one embodiment of the invention. The method 700 may be performed by the motion detector 150 of FIG. 1.

As shown, the method 700 begins at step 710, where a light sink 164 detects light emitted from a plurality of light sources 162. For example, the light sink d0 of FIG. 2 may detect light 156 emitted from light sources e0 through e10 of FIG. 2. At step 720, the motion detector 150 analyzes the detected light 156. For example, the motion detector 150 may perform Fourier analysis on the detected light 156 (e.g., to generate a power spectrum graph 320 for the detected light 156).

At step 730, the motion detector 150 computes a change in 3D spatial position of the light sink 164 based on the analysis. The motion detector 150 may also compute a change in 3D spatial position (e.g., coordinates and orientation) of the subject 202 based on the computed change in spatial position of one or more light sinks 164. In another embodiment, the motion detector 150 may also take into account one or more spatial positions (e.g., initial, known 3D coordinates) of a light sink 164 to compute a change in 3D spatial position of the light sink 164. Further, the motion detector 150 may also compute 3D coordinates for one or more light sinks 164 and for the subject 202. In computing the change in 3D spatial position (either of the subject 202 or of the light sink 164), the motion detector 150 may also take into account any movement of the light sources 162 (i.e., if the positions of the light sources 162 are not fixed during an MRI scan). After step 730, the method 700 terminates.

Those skilled in the art will recognize, for example, that embodiments of the invention may be adapted to support networks other ways of representing light 156 detected by detectors 164, other ways of arranging emitters 162 in an MRI environment, other ways of determining emitter frequencies 154, other ways of analyzing detected light 156, other ways of securing one or more detectors 164 on a subject 202, and other ways of determining spatial location (and/or changes thereof) of detectors 164 and subjects 202.

Advantageously, embodiments of the invention capture motion information in an MRI environment. In one embodiment, a light sink in the MRI environment may detect light emitted from a plurality of light sources. Each of the plurality of light sources may emit light of a different frequency. Further, each of the plurality of light sources may be located at a different spatial position in the MRI environment. A motion detector may analyze the detected light. The motion detector may compute a change in spatial position of the light sink based on the analysis, the different frequencies, and/or the different spatial positions. Further, the one or more light sinks may be detachably fastened to a subject. The motion detector may compute a change in spatial position of the subject during an MRI scan, based on the computed changes in spatial positions of one or more light sinks. Further, the motion detector may compute spatial positions of one or more light sinks and/or the subject. In addition, the motion detector may capture motion information in real time. The motion detector may also compute spatial positions, and changes thereof, efficiently and accurately. In particular, the motion detector 150 may detect motion more accurately than could video-based approaches. Further, the motion detector 150 may correct a wider variety of motion than could (pure) post-processing approaches. The motion detector 150 may also be used to enhance post-processing approaches to motion correction.

While the foregoing is directed to embodiments of the present invention, other and further embodiments of the invention may be devised without departing from the basic scope thereof, and the scope thereof is determined by the claims that follow.

What is claimed is:

1. A computer-implemented method for capturing motion information in a magnetic resonance imaging (MRI) environment, based on light sources having different frequencies and different spatial positions, the method comprising:
   detecting, by a light sink in the MRI environment, light emitted from a plurality of light sources, wherein each of the plurality of light sources emit light of a different frequency of a plurality of frequencies, wherein each of the plurality of light sources is located at a different spatial position of a plurality of spatial positions in the MRI environment, and wherein the light sink is detachably fastened to a subject;
   analyzing the detected light to determine, by operation of one or more computer processors, a change in spatial position of the light sink; and
   determining a change in spatial position of the subject during an MRI scan, based on the determined change in spatial position of the light sink.

2. The computer-implemented method of claim 1, wherein the method further comprises:
   receiving an MRI image of the subject during the MRI scan; and
   correcting a motion in the received MRI image, based on the determined change in spatial position of the subject.

3. The computer-implemented method of claim 1, wherein analyzing the detected light comprises determining a change in peak frequency of the detected light.

4. The computer-implemented method of claim 3, wherein determining a change in peak frequency of the detected light includes decomposing, via a fast Fourier transform, the detected light into frequency components of the detected light.

5. The computer-implemented method of claim 1, wherein the method further comprises:
   determining the plurality of frequencies for the plurality of light sources; and
   determining the plurality of spatial positions for the plurality of light sources.

6. The computer-implemented method of claim 1, wherein the light sink is an open-ended tip of an optical fiber cable, wherein each of the plurality of light sources is an open-ended tip of an optical fiber cable, and wherein the location of each of the plurality of light sources is fixed in the MRI environment.

7. A computer-readable memory containing a program which, when executed, performs an operation for capturing motion information in a magnetic resonance imaging (MRI) environment, based on light sources having different frequencies and different spatial positions, the operation comprising:
   detecting, by a light sink in the MRI environment, light emitted from a plurality of light sources, wherein each of the plurality of light sources emit light of a different frequency of a plurality of frequencies, wherein each of the plurality of light sources is located at a different spatial position of a plurality of spatial positions in the MRI environment, and wherein the light sink is detachably fastened to a subject;
   analyzing the detected light to determine, by operation of the one or more computer processors, a change in spatial position of the light sink; and
   determining a change in spatial position of the subject during an MRI scan, based on the determined change in spatial position of the light sink.

8. The computer-readable memory of claim 7, wherein the operation further comprises:
   receiving an MRI image of the subject during the MRI scan; and
   correcting a motion in the received MRI image, based on the determined change in spatial position of the subject.

9. The computer-readable memory of claim 7, wherein analyzing the detected light comprises determining a change in peak frequency of the detected light.

10. The computer-readable memory of claim 9, wherein determining a change in peak frequency of the detected light includes decomposing, via a fast Fourier transform, the detected light into frequency components of the detected light.

11. The computer-readable memory of claim 7, wherein the operation further comprises:
    determining the plurality of frequencies for the plurality of light sources; and
    determining the plurality of spatial positions for the plurality of light sources.

12. The computer-readable memory of claim 7, wherein the light sink is an open-ended tip of an optical fiber cable, wherein each of the plurality of light sources is an open-ended tip of an optical fiber cable, and wherein the location of each of the plurality of light sources is fixed in the MRI environment.

13. A system for capturing motion information in a magnetic resonance imaging (MRI) environment, based on light sources having different frequencies and different spatial positions, the system comprising:
    a processor; and
    a memory containing a program, which when executed by the processor is configured to perform an operation comprising:
       detecting, by a light sink in the MRI environment, light emitted from a plurality of light sources, wherein each of the plurality of light sources emit light of a different frequency of a plurality of frequencies, wherein each of the plurality of light sources is located at a different spatial position of a plurality of spatial positions in the MRI environment, and wherein the light sink is detachably fastened to a subject;
       analyzing the detected light to determine, by operation of the one or more computer processors, a change in spatial position of the light sink; and determining a change in spatial position of the subject during an MRI scan, based on the determined change in spatial position of the light sink.

14. The system of claim 13, wherein the operation further comprises:
receiving an MRI image of the subject during the MRI scan; and
correcting a motion in the received MRI image, based on the determined change in spatial position of the subject.

15. The system of claim 13, wherein analyzing the detected light comprises determining a change in peak frequency of the detected light.

16. The system of claim 15, wherein determining a change in peak frequency of the detected light includes decomposing, via a fast Fourier transform, the detected light into frequency components of the detected light.

17. The system of claim 13, wherein the operation further comprises:
determining the plurality of frequencies for the plurality of light sources; and
determining the plurality of spatial positions for the plurality of light sources.

18. The system of claim 13, wherein the light sink is an open-ended tip of an optical fiber cable, wherein each of the plurality of light sources is an open-ended tip of an optical fiber cable, and wherein the location of each of the plurality of light sources is fixed in the MRI environment.

19. The computer-implemented method of claim 1, wherein the change in spatial position of the subject is determined in order to capture motion information in the MRI environment, based on light sources having different frequencies and different spatial positions.

20. The computer-implemented method of claim 19, wherein the change in spatial position of the light sink is determined based further on an initial spatial position of the light sink, different from a final spatial position of the light sink, wherein the change in spatial position of the subject during the MRI scan is determined based further on an initial spatial position of the subject, different from a final spatial position of the subject.

21. The computer-implemented method of claim 20, wherein analyzing the detected light comprises determining a change in peak frequency of the detected light, wherein determining the change in peak frequency of the detected light includes decomposing, via a fast Fourier transform, the detected light into frequency components of the detected light.

22. The computer-implemented method of claim 21, further comprising:
receiving an MRI image of the subject during the MRI scan;
correcting a motion in the received MRI image, based on the determined change in spatial position of the subject;
determining the plurality of frequencies for the plurality of light sources; and
determining the plurality of spatial positions for the plurality of light sources.

23. The computer-implemented method of claim 22, further comprising determining 3D coordinates of the light sink based on the analysis, wherein determining the 3D coordinates of the light sink based on the analysis comprises:
determining, based on the analysis, a plurality of spatial distances including a respective spatial distance of the light sink from each of the plurality of light sources; and
determining an intersection of the plurality of spatial distances of the light sink from the plurality of light sources;
wherein the light sink is an open-ended tip of an optical fiber cable, wherein each of the plurality of light sources is an open-ended tip of an optical fiber cable, and wherein the location of each of the plurality of light sources is fixed in the MRI environment.

24. The computer-implemented method of claim 23, wherein each light source comprises an emitter, wherein the method is performed by a motion detector application, wherein the motion detector application comprises:
(i) a position manager component configured to set emitter positions based on user input specifying the emitter positions;
(ii) a frequency manager component configured to set emitter frequencies based on user input specifying the emitter frequencies;
(iii) an input manager component configured to receive data representing the detected light;
(iv) a light analyzer component configured to decompose, via the fast Fourier transform, the detected light into frequency components of the detected light; and
(v) a motion calculator component configured to:
(A) responsive to a first request, determine the change in spatial position of the subject during the MRI scan, based on the determined change in spatial position of the light sink; and
(B) responsive to a second request different from the first request, determine 3D coordinates of the light sink, based on the analysis.

* * * * *